US00PP22866P3

(12) United States Plant Patent
Egger

(10) Patent No.: US PP22,866 P3
(45) Date of Patent: Jul. 17, 2012

(54) *SEDUM* PLANT NAMED 'CHOCOLATE DROP'

(50) Latin Name: ***Sedum* sp.**
Varietal Denomination: Chocolate Drop

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 309 days.

(21) Appl. No.: 12/798,839

(22) Filed: Apr. 12, 2010

(65) Prior Publication Data

US 2011/0252533 P1 Oct. 13, 2011

(51) Int. Cl.
*A01H 5/00* (2006.01)

(52) U.S. Cl. ..... Plt./479

(58) Field of Classification Search ..... Plt./479
See application file for complete search history.

(56) References Cited

U.S. PATENT DOCUMENTS

PP16,831 P2 * 7/2006 de Buck ..... Plt./479
PP18,168 P2 * 10/2007 Degenhardt ..... Plt./479

OTHER PUBLICATIONS

Anonymous. "*Sedum* 'Chocolate Drop'" Terra Nova Nurseries available at http://www.terranovanurseries.com/cart/product_info.php?products_id=206 accessed Sep. 30, 2011.*

* cited by examiner

*Primary Examiner* — Wendy C Haas
(74) *Attorney, Agent, or Firm* — Klarquist Sparkman, LLP

(57) ABSTRACT

A new and distinct hybrid of *Sedum* plant substantially as shown and described, with medium size, oval, glossy red brown leaves with cut edges, a low compact habit, showy maroon stems, dull rose pink flowers, and excellent vigor.

1 Drawing Sheet

Botanical denomination: *Sedum* sp.

Variety designation: 'Chocolate Drop'.

Parentage: *S. spectabile* 'Neon' (unpatented)×*S. telephium* dark leaf.

The present invention relates to a new and distinct cultivar of *Sedum* and given the cultivar name of 'Chocolate Drop'. *Sedum* is in the family Crassulaceae. *Sedum* 'Chocolate Drop' originated from an open pollinated cross between *Sedum spectabile,* 'Neon', unpatented, as the seed parent and a proprietary, unpatented dark leaf *Sedum telephium* as the pollen parent. Compared to *Sedum spectabile* 'Neon', the new cultivar has red brown rather than blue green leaves and duller smaller flower clusters. Compared to the *Sedum telephium* pollen parent, the new cultivar has a shorter denser habit, larger flower clusters, and rounder and lighter brown leaves. There are no similar commercial varieties known to the inventor.

This new and unique *Sedum* is distinguished by:

1. medium size, oval, glossy red brown leaves with cut edges,
2. low compact habit,
3. showy maroon stems,
4. dull rose pink flowers,
5. and excellent vigor.

This new cultivar has been reproduced only by asexual propagation (division, cuttings, and tissue culture). Each of the progeny exhibits identical characteristics to the original plant. Asexual propagation by cuttings, division and tissue culture using standard techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a two-year-old *Sedum* 'Chocolate Drop' growing in the ground in the garden fields on September 1$^{st}$ in Canby, Oreg.

DETAILED PLANT DESCRIPTION

The following is a detailed description of the new *Sedum* hybrid based on observations of one-year-old specimen grown in a the ground in full sun in the garden in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, 5$^{th}$ edition.

Plant:

*Type.*—Herbaceous perennial.
*Hardiness.*—USDA Zone 4 to 9.
*Size.*—Grows to 23 cm tall from the ground to the top of the foliage and 23 cm wide.
*Habit.*—Ascending. clumping.
*Vigor.*—Excellent.

Stem:

*Size.*—Grows to 15 cm and 8 mm wide.
*Number.*—Plants have between 4 and 12 stems.
*Internodes.*—3 to 8 mm long.
*Surface.*—Glabrous, shiny.
*Color.*—Greyed Purple 187B.

Leaf:

*Type.*—Simple.

*Arrangement.*—Opposite.

*Shape.*—Elliptic.

*Apex.*—Obtuse.

*Base.*—Truncate to slightly auriculate.

*Venation.*—Pinnate.

*Margins.*—Dentate.

*Blade size.*—Grows to 7 cm long and 3.5 cm wide.

*Surface.*—Glabrous, glossy.

*Texture.*—Thick, succulent.

*Petiole.*—Leaves sessile.

*Leaf color.*—Topside Brown 200A lightening to Yellow Green 147A tinted Brown 200A where shaded, main vein Greyed Purple 187A; bottom side Greyed Purple 187A where in sun and Yellow Green 147A tinted Greyed Purple 187A where shaded, main vein Greyed Purple 187B.

Inflorescence:

*Type.*—Terminal, corymbose, umbel-like.

*Size of inflorescence.*—Grows to 9.5 cm wide and 7 cm deep.

*Number of flowers.*—About 250 per stem.

*Peduncle.*—Grows to 6 cm tall and 2.5 mm wide, Greyed Purple 187A, glabrous.

*Branching.*—3 main branches per stem.

*Bloom period.*—July in Canby, Oreg.

Flower bud:

*Size.*—3 mm wide, 6 mm long.

*Description.*—Ovoid.

*Color.*—Top ⅔ Greyed Green 191A and Greyed Purple 187C, bottom ⅓ Green White 157D.

Flower:

*Type.*—Complete, actinomorphic.

*Shape.*—Rotate.

*Size.*—7 mm deep and 9 mm wide.

*Color.*—Red 54D with center Red Purple 58A.

*Corolla description.*—9 mm wide and 5 mm deep, 5 petals, each lanceolate, 5 mm long and 2 mm wide, entire, glabrous on both sides, tip keeled, White NN155D mottled with Red Purple 61A on both sides, back side near tip Greyed Green 191A.

*Calyx description.*—Stellate, 2 mm deep and 3 mm wide, 5 small narrow lobes, divided ⅚ to the base, 1.5 mm long and 1 mm wide at the base, entire, acute, glabrous and Greyed Green 189A on both sides.

*Stamen description.*—10 in number, 6 mm long, filaments 5.5 mm long, Red Purple 60A, anthers undehisced Greyed Purple 185A, pollen Yellow Orange 18C.

*Pistil description.*—5 separate prominent carpels, each 4 mm deep and 1 mm wide, Red Purple 58A.

*Fragrance.*—None.

*Lastingness.*—Each inflorescence lasts for about 3 weeks.

Fruit:

*Type.*—Ventrally dehiscent follicle, erect, attenuate.

*Fertility.*—Unknown, none seen.

Seed.—None seen.

Disease and pest resistance or tolerance: All *Sedum* species are susceptible to root rots with poor drainage. They are also susceptible to mealybug, scale, slugs and snails. None of these insect problems have been noted on the new variety.

I claim:

1. A new and distinct hybrid of *Sedum* plant as herein illustrated and described.

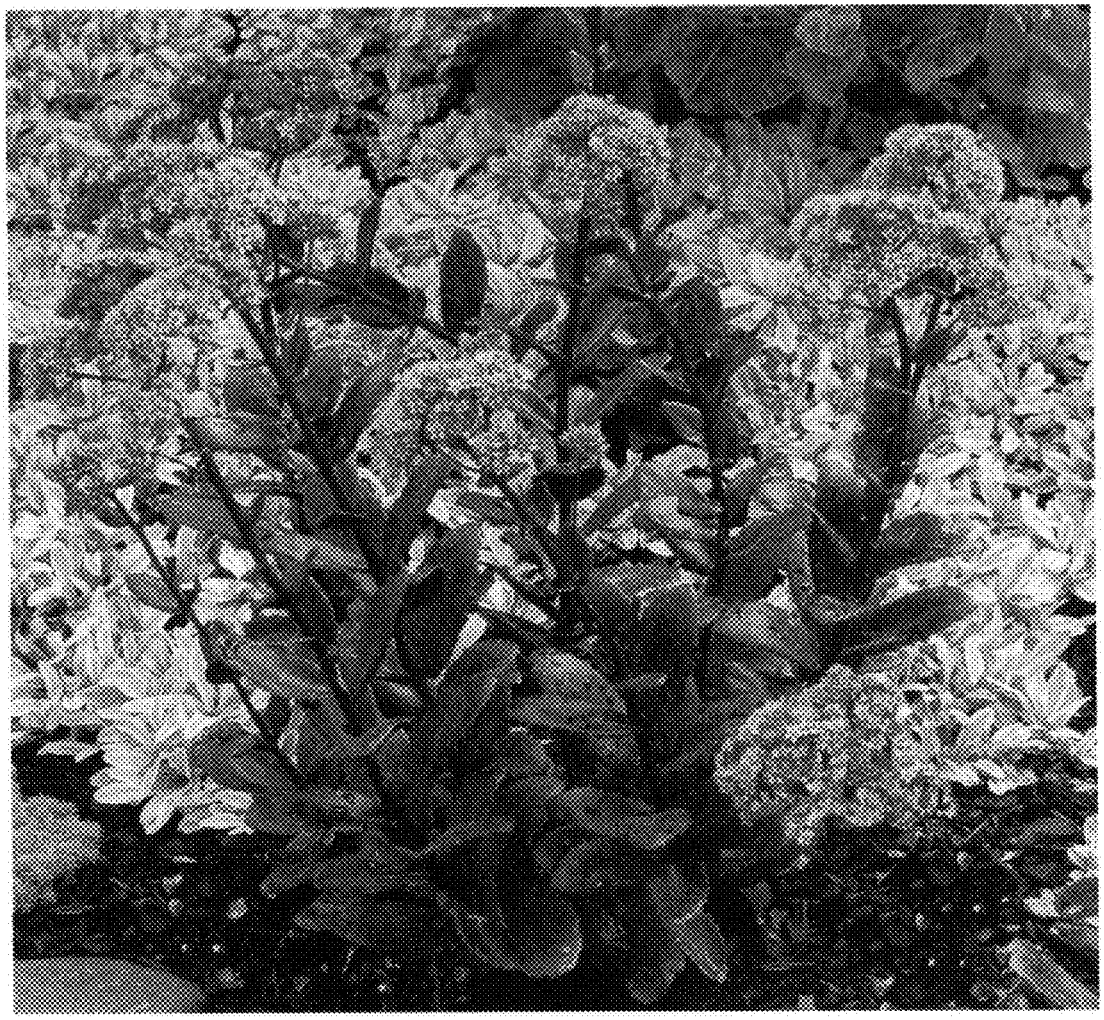

* * * * *